United States Patent
Smith et al.

(10) Patent No.: US 8,114,100 B2
(45) Date of Patent: Feb. 14, 2012

(54) SAFETY FASTENER FOR TISSUE APPOSITION

(75) Inventors: Richard C. Smith, Milford, OH (US); John P. Measamer, Cincinnati, OH (US); Michael S. Cropper, Edgewood, KY (US); Richard F. Schwemberger, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 441 days.

(21) Appl. No.: 11/567,259

(22) Filed: Dec. 6, 2006

(65) Prior Publication Data

US 2008/0140095 A1  Jun. 12, 2008

(51) Int. Cl.
*A61B 17/122* (2006.01)

(52) U.S. Cl. ........ 606/151; 606/153; 606/219; 606/220; 24/706.4; 24/707.7; 24/710.4

(58) Field of Classification Search .............. 606/72, 606/75, 139–158, 219–220, 300; 27/19–50; 24/706.2, 706.4–706.9, 707.2–707.3, 707.7, 24/709.5–709.6, 710.4–710.5; 411/439; 623/23.72

See application file for complete search history.

(56) References Cited

U.S. PATENT DOCUMENTS

| | | | | |
|---|---|---|---|---|
| 1,275,088 A | * | 8/1918 | Ramos | 24/710.4 |
| 1,857,158 A | * | 5/1932 | Maloney | 248/685 |
| 2,592,506 A | * | 4/1952 | Yanagihara | 24/707.7 |
| 2,598,198 A | * | 5/1952 | Todd | 24/710 |
| 2,644,211 A | * | 7/1953 | Sumner | 24/707.7 |
| 3,244,444 A | * | 4/1966 | Bisbing | 292/306 |
| 3,955,462 A | * | 5/1976 | Thorsman | 411/439 |
| 4,005,507 A | * | 2/1977 | Yamazaki | 24/351 |
| 5,393,184 A | * | 2/1995 | Beeuwkes, III | 411/469 |
| 5,549,621 A | | 8/1996 | Bessler et al. | |
| 5,649,937 A | * | 7/1997 | Bito et al. | 606/139 |
| 6,276,030 B1 | * | 8/2001 | Smith | 24/115 G |
| 6,494,888 B1 | | 12/2002 | Laufer et al. | |
| 7,004,703 B2 | * | 2/2006 | Johnson et al. | 411/439 |
| 2002/0082625 A1 | * | 6/2002 | Huxel et al. | 606/153 |
| 2003/0065340 A1 | * | 4/2003 | Geitz | 606/151 |
| 2004/0059358 A1 | * | 3/2004 | Kortenbach et al. | 606/153 |
| 2005/0101974 A1 | * | 5/2005 | Burbank et al. | 606/151 |
| 2006/0282084 A1 | * | 12/2006 | Blier et al. | 606/72 |

FOREIGN PATENT DOCUMENTS

| | | |
|---|---|---|
| CA | 2549220 | 3/2006 |
| EP | 1547528 | 6/2005 |

* cited by examiner

*Primary Examiner* — Corrine M McDermott
*Assistant Examiner* — Mark Mashack
(74) *Attorney, Agent, or Firm* — Nutter McClennen & Fish LLP

(57) ABSTRACT

Methods and devices for fastening tissue are provided. In one exemplary embodiment, a tissue fastener is provided and includes a male fastening member having a base plate with at least one post extending therefrom and having a tissue-piercing tip. A protective member is coupled to the male fastening member and is movable between an open position in which the tissue-piercing tip is enclosed within the protective member such that the tissue-piercing tip is prevented from penetrating tissue, and a compressed position in which the tissue-piercing tip is exposed to penetrate tissue. A female fastening member is configured to mate to the male fastening member and to engage tissue therebetween.

19 Claims, 11 Drawing Sheets

SAFETY FASTENER FOR TISSUE APPOSITION

FIELD OF THE INVENTION

The present invention relates to methods and devices for fastening tissue, and in particular to a fastener having a safety feature.

BACKGROUND OF THE INVENTION

Gastroesophageal reflux disease (GERD) or persistent heartburn is caused by an improper relaxation of the lower esophageal sphincter (LES) that allows the frequent regurgitation of acidic stomach contents into the esophagus. If left untreated, chronic reflux may cause esophageal stricture, bleeding ulcers, perforation, and scarring. Continued reflux may cause changes in the cells that make up the esophagus, which can in turn lead to cancer. The current mode of treatment is primarily pharmacological, starting with antacids and progressing to proton pump inhibitors (PPIs). The pharmacological treatment ends with double and triple dosing of PPIs. At the point that the patient is not responding to PPIs, a surgical procedure to tighten the LES and make it less compliant is often recommended.

One procedure to tighten the LES involves wrapping a fundus of the stomach around the lower end of the esophagus and fastening it in place. This was traditionally accomplished by open surgery using sutures to secure the plicated fundus of the stomach around the esophagus without penetrating the stomach. More recently, laparoscopic surgery has become standard, and in some laparoscopic procedures surgical fasteners are used with an endoscopic applicator. Several different fastener designs have been developed.

Some of these designs include an applier with a two piece fastener. A male piece of the fastener includes several straight elongate needles extending perpendicularly outward from a base and generally parallel to each other. A female piece of the fastener includes a receiver element having openings positioned for receiving the needles of the male piece and a mating element for holding the needles in place once received in the openings. In use, tissue is gathered, and the needles of the male piece are pushed through the gathered tissue and into the openings of the female piece to hold the tissue fastener in place. This design works fine for a specific range of tissue thicknesses, however, if tissue outside this range is encountered there will be too little compression (thin tissue) to promote serosa to serosa healing, or too much compression (thick tissue) resulting in tissue necrosis. In addition, the needles are exposed when the applier jaws are open, increasing the risk of collateral tissue damage during the procedure.

Thus, there remains a need for an improved surgical fastener that overcomes some of the aforementioned drawbacks.

SUMMARY OF THE INVENTION

The present invention generally provides methods and devices for fastening tissue. In one exemplary embodiment, a tissue fastener is provided and includes a male fastening member having a base plate with at least one post extending therefrom and having a tissue-piercing tip. A protective member is coupled to the male fastening member and is movable between an open position in which the tissue-piercing tip is enclosed within the protective member such that the tissue-piercing tip is prevented from penetrating tissue, and a compressed position in which the tissue-piercing tip is exposed to penetrate tissue. A female fastening member is configured to mate to the male fastening member and to engage tissue therebetween.

In one embodiment, the male fastening member can have at least one post extending substantially perpendicular to a surface of the base plate. A mating element can be formed on the post and configured to mate to the female fastening member. The protective member can include at least one bore formed therethrough and adapted to receive the post. In use, the protective member can be adapted to move from the open position to the compressed position as the post is penetrated through tissue. In another embodiment, the male fastening member can include a biasing element configured to bias the protective member to the open position. The biasing element can be, for example, a U-shaped spring that is mated to and extends between the base plate and the protective member, or a coil spring that is disposed around the post(s) and extends between the base plate and protective member. In another embodiment, the biasing element can be in the form of a compressible body surrounding the post(s). The compressible body can be adapted to be penetrated by the tissue-piercing tip on the at least one post when the protective member is moved to the compressed position.

In another embodiment, a tissue fastener is provided having a base member with first and second tissue-penetrating elements formed thereon and a protective member movably coupled to the first and second tissue-penetrating elements. The protective member is adapted to prevent the first and second tissue-penetrating elements from penetrating through tissue until the protective member is advanced against tissue to be penetrated by the first and second-tissue penetrating members. In an exemplary embodiment, the protective member includes a plate with first and second bores formed therethrough that are adapted to receive the first and second tissue-penetrating elements. In use, the protective member can be adapted to move between a first position in which the first and second tissue-penetrating elements are enclosed within the protective member such that the first and second tissue-penetrating elements are prevented from penetrating tissue, and a second position in which the first and second tissue-penetrating elements are exposed to penetrate tissue. The device can further include a closure mechanism adapted to mate to the first and second tissue-penetrating elements to engage tissue between the base member and the closure mechanism.

Also disclosed herein are methods for fastening tissue. In one embodiment, the method can include inserting a tissue-engaging fastener into a body cavity with the tissue-engaging fastener having a protective member that prevents collateral tissue damage during insertion of the tissue-engaging fastener. A male fastening member and a female fastening member can be positioned on opposed sides of tissue to be fastened and they can be mated to engage tissue therebetween. In an exemplary embodiment, the protective member moves as the tissue is engaged to allow the male fastening member to penetrate through the tissue and to mate with the female fastening member. In an exemplary embodiment, the protective member has at least one bore formed therethrough that can receive a tissue-penetrating member formed on the male fastening member as the tissue-engaging fastener is inserted into the body cavity. The protective member can prevent the tissue-penetrating member from penetrating through tissue during insertion of the tissue-engaging fastener to thereby prevent collateral tissue damage. In another exemplary embodiment, a biasing element can apply a biasing force to the protective element to bias it to a first position in which the tissue-penetrating member is enclosed within the protective member such that the tissue-penetrating member is prevented from penetrating tissue. The biasing element can further provide a constant compression force to engage tissue held between the protective member and the female fastening member.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for fastening tissue. In general, the methods and devices allow tissue to be fastened while preventing collateral tissue damage. In one exemplary embodiment, a tissue fastening device is provided having a male fastening member and a female fastening member designed to engage tissue therebetween. The device can include a protective member that is adapted to prevent collateral tissue damage as the fastener is inserted into a body cavity and prior to deployment. The protective member can also or alternatively be adapted to provide a constant compression force to engaged tissue. A person skilled in the art will appreciate that the methods and devices disclosed herein can be configured for use in virtually any medical procedure in which it is desirable to attach two tissue surfaces to one another, however in certain exemplary embodiments the methods and devices are used to fasten tissue in order to tighten the lower esophageal sphincter to prevent gastroesophageal reflux disease.

Figure 1A:
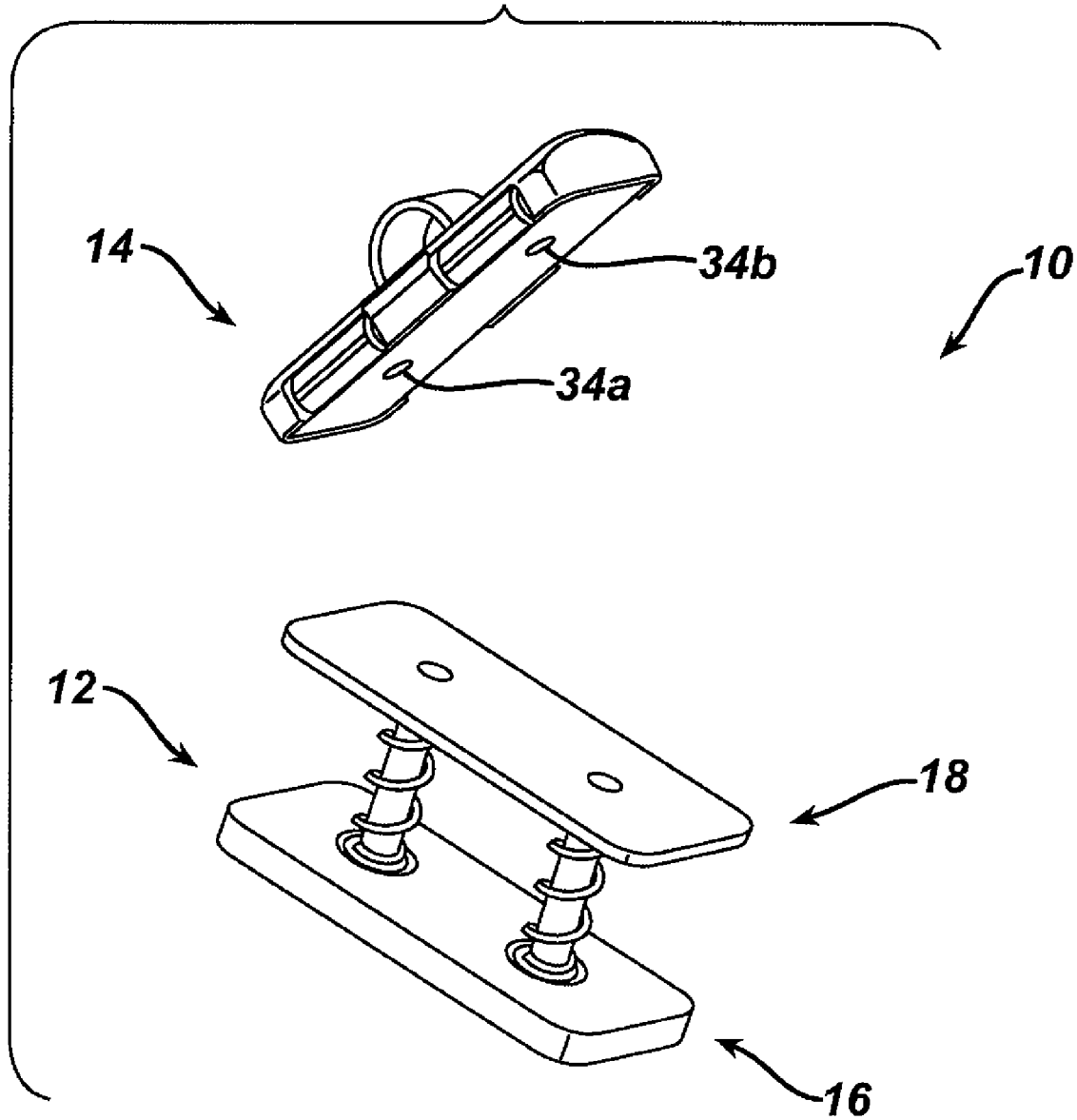
FIG. 1A is a perspective view of one exemplary embodiment of a tissue fastening device having a male fastening member and a female fastening member, showing the members in an unmated configuration.

FIG. 1A illustrates one exemplary embodiment of a tissue-fastening device 10 having a protective member 18 for preventing collateral tissue damage, and/or for providing a constant compression force to engaged tissue. In the illustrated embodiment, the device generally includes a male fastening member 12 and a female fastening member 14 configured to engage tissue therebetween. As shown, the male fastening member 12 includes a base plate 16 with first and second tissue-penetrating members 20a, 20b having the protective member 18 coupled thereto. In use, the protective member 18 can protect the tissue from the tissue-penetrating members 20a, 20b until the device is deployed. When deployed, as the female fastening member 14 is mated to the male fastening member 12, the tissue positioned therebetween will move the protective member 18 to expose the tissue-penetrating members 20a, 20b, thus allowing the tissue-penetrating members 20a, 20b to penetrate through the tissue and mate to the female fastening member 14.

Figure 1B:
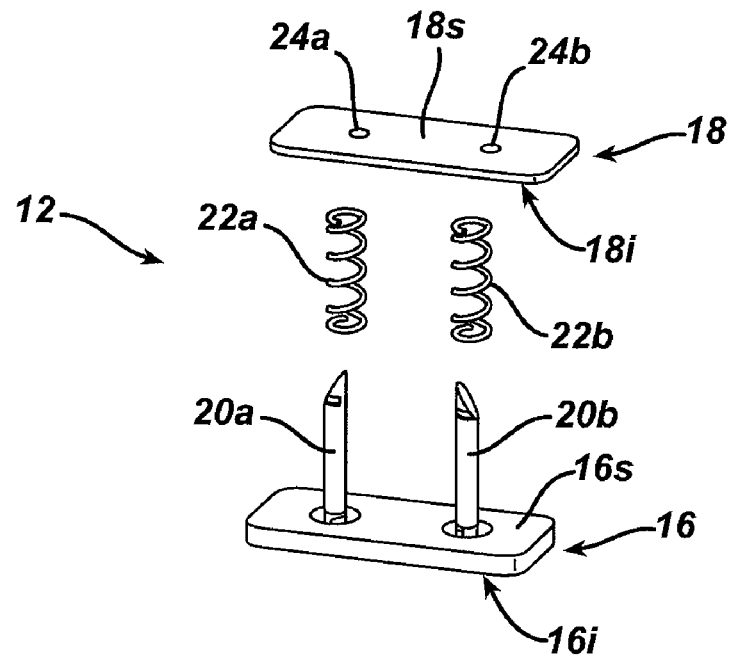
FIG. 1B is an exploded view of the male fastening member of FIG. 1A.
Figure 1C:
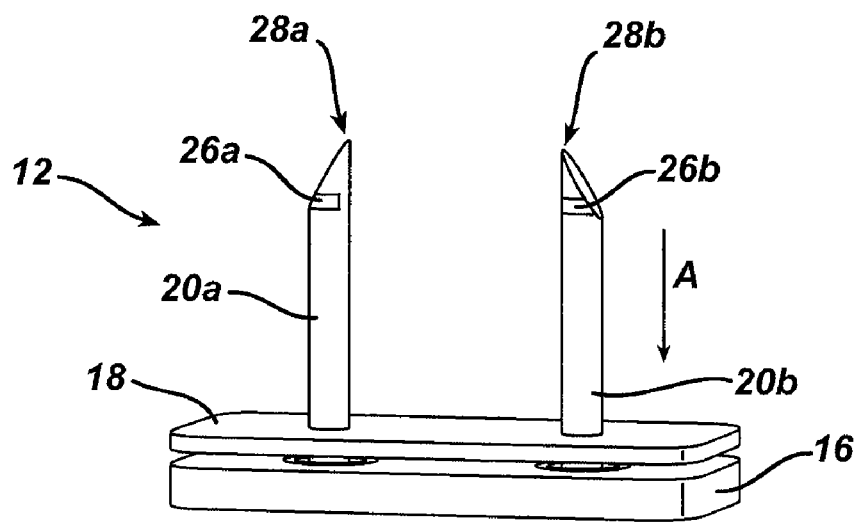
FIG. 1C is a perspective view of the male fastening member of FIG. 1A, showing the protective member in a compressed position.

FIGS. 1B and 1C illustrate the male fastening member 12 in more detail and as shown, the male fastening member 12 generally includes a base plate 16 with opposed superior and inferior surfaces 16s, 16i. The base plate 16 can have a variety of configurations, shapes, and sizes, but in one exemplary embodiment the base plate 16 is rigid and has a generally rectangular shape. The dimensions of the base plate 16 can also vary, but it is preferably of a size and shape that is sufficient to grasp tissue. As indicated above, the male fastening member 12 can include one or more tissue-penetrating members formed thereon and adapted to penetrate through tissue. In an exemplary embodiment, as shown, the male fastening member 12 includes first and second tissue-penetrating members 20a, 20b in the form of elongated posts that are spaced a distance apart from one another and that extend parallel to each other in a direction substantially perpendicular to the superior surface 16s of the base plate 16. The first and second tissue-penetrating members 20a, 20b can be integrally formed with the base plate 16 or the first and second tissue-penetrating members 20a, 20b can be formed from one or two separate elements that are mated to the base plate 16. As further shown in FIGS. 1B and 1C, each tissue-penetrating member 20a, 20b can include a piercing tip 28a, 28b that is tapered to form a sharp point for penetrating tissue. The first and second tissue-penetrating members 20a, 20b can also each have a mating element for mating to the female fastening member 14. In one exemplary embodiment, the mating element is a notch 26a, 26b spaced a distance from the piercing tip 28a, 28b and adapted to be received within a corresponding groove formed on the female fastening member 14, as will be discussed in more detail below. A person skilled in the art will appreciate that a variety of other technologies can be used to mate the male and female fastening members 12, 14. Moreover, the tissue-penetrating members 20a, 20b can have a variety of other configurations, and they can be positioned at various locations and extend at various orientations relative to the base plate 16.

The male fastening member 12 can further include a protective member 18 that is adapted to prevent collateral tissue damage as the fastener is inserted into a body cavity, and/or that is adapted to provide a constant compression force to engaged tissue. The protective member 18 can have a variety of shapes and configurations, but it is preferably adapted to surround and shield the piercing tips 28a, 28b of the tissue-penetrating members 20a, 20b prior to deployment of the device. In one exemplary embodiment, as shown in FIGS. 1A-1C, the protective member 18 can be in the form of a plate that is movably connected to the base plate 16. While the dimensions of the protective member 18 can vary, it preferably has a size and shape that is sufficient to compress tissue. In one embodiment, the protective member 18 can be generally rectangular in shape with superior and inferior surfaces 18s, 18i. The protective member 18 can also have one or more openings that are adapted to receive the tissue-penetrating members 20a, 20b on the male fastening member. In the embodiment shown in FIGS. 1A-1C, the protective member has two openings 24a, 24b spaced a distance apart from each other and configured to receive the first and second tissue-penetrating members 20a, 20b of the male fastening member 12. When mated to the tissue-penetrating members 20a, 20b, the protective member 18 will be positioned at a height above and parallel to the superior surface 16s of the base plate 16. The openings 24a, 24b preferably have a size and shape that is sufficient to slidably engage the tissue-penetrating members 20a, 20b such that the protective member 18 will not decouple from the male fastening member 12 during use of the device. The protective member 18 also preferably has a thickness extending between the superior and inferior surfaces 18s, 18i that is sufficient to allow the piercing tips 28a, 28b to be fully disposed within and surrounded by the openings 24a, 24b.

The protective member 18 can also be formed from a variety of materials, including bioabsorbable and non-absorbable materials. Exemplary materials include various metals, such as titanium and stainless steel, and various non-absorbable polymers, such as polytetrafluoroethylene (PTFE), polyetheretherketone (PEEK).

The male fastening member 12 can also include a biasing element disposed between the base plate 16 and the protective member 18 so as to bias the protective member 18 to an open position. In one exemplary embodiment as shown in FIG. 1C, the biasing element can be in the form of first and second springs 22a, 22b, each of which surrounds the first and second tissue-penetrating members 20a, 20b and extends between the base plate 16 and the protective member 18. In use, each spring 22a, 22b maintains the protective member 18 in an open position in which the protective member 18 surrounds the piercing tips 28a, 28b. When tissue is placed between the protective member 18 and the female fastening member 14, the force applied to the protective member 18 will overcome the biasing force of the springs 22a, 22b, thereby moving the protective member 18 in a direction A towards the base plate 16, so as to expose the piercing tips 28a, 28b which thus penetrate through the tissue. The springs 22a, 22b will continue to provide a biasing force to the protective member 18 even after the male and female fastening members 12, 14 are mated. This allows the protective member 18 to provide a constant compression force to the tissue engaged therebetween, thereby maintaining contact between tissue surfaces but preventing tissue necrosis.

Figure 2A:
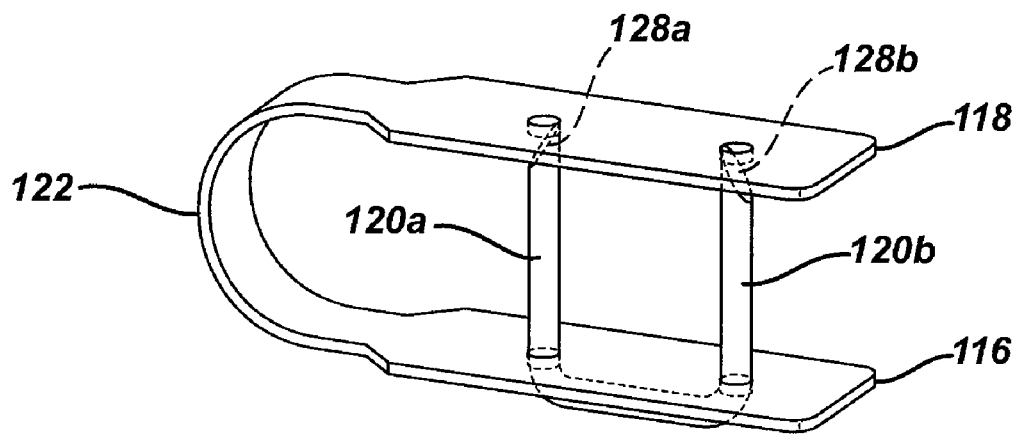
FIG. 2A is a perspective view of another embodiment of a protective member and biasing element for use with a tissue fastening device.

FIG. 2A illustrates another exemplary embodiment of a biasing element for biasing the protective member to the open position. In this embodiment, the biasing element is in the form of a spring 122 that is mated to and extends between the protective member 118 and the base plate 116. In particular, the illustrated spring 122 is integrally formed with the protective member 118 and the base plate 116, such that the protective member 118, spring 122, and base plate 116 are formed from a single U-shaped member. In use, the spring 122 is configured to be compressed when a force is applied to the protective member 118 to allow the protective member 118 to move toward the base plate 116, thereby exposing the piercing tips 128a, 128b on the first and second tissue-penetrating members 120a, 120b. The protective member 118, spring 122, and base plate 116, or portions thereof, can be made from a variety of materials that allow the spring 122 to deform when a force is applied to the protective member. Exemplary materials include, by way of non-limiting example, shape memory materials, such as Nitinol.

Figure 2B:
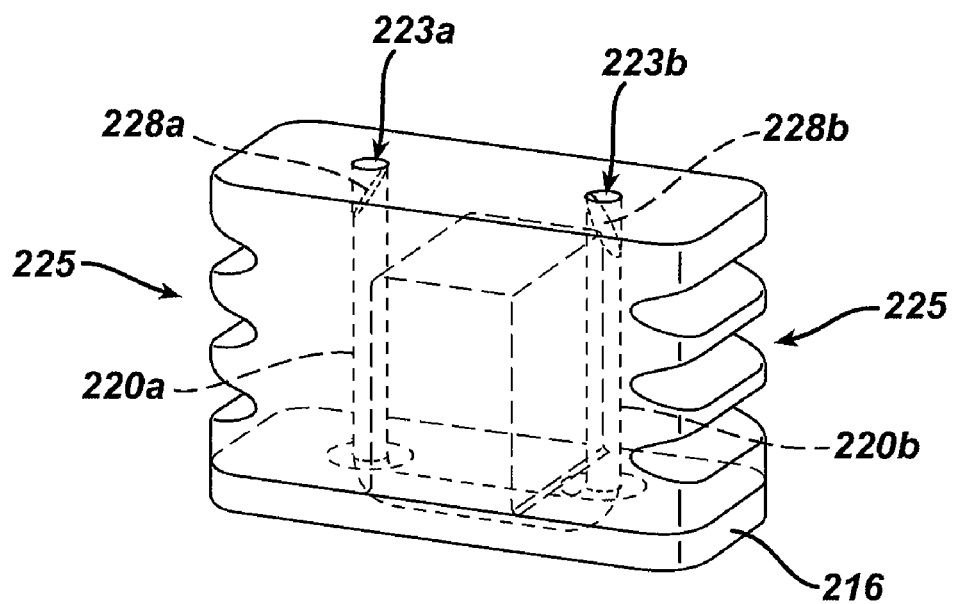
FIG. 2B is a perspective view of another embodiment of a biasing element in the form of a compressible body that is disposed around tissue-penetrating elements on a male fastening member.

FIG. 2B illustrates yet another embodiment of a biasing element for biasing the protective member to the open position. In this embodiment, the biasing element in the form of a compressible body 222 that surrounds the first and second tissue-penetrating members 220a, 220b, including the piercing tips 228a, 228b, and that is disposed between the base plate 216 and the protective member 218. The compressible body 222 can have a variety of shapes and sizes, but in the illustrated embodiment the compressible body 222 is substantially solid and has a rectangular shape such that is occupies the entire space between the base plate 216 and the protective member 218. The body 222 can, however, include features to facilitate compression thereof. For example, as shown in FIG. 2B, the body 222 includes a series of cut-outs or ridges 225 formed in opposed ends thereof to facilitate compression. The compressible body 222 can include first and second lumens 223a, 223b extending partially or fully therethrough for receiving the first and second tissue-penetrating members 220a, 220b. Where the lumens 223a, 223b do not extend fully through the body 222, the body 222 can be configured to allow the piercing tips 228a, 228b to penetrate therethrough when the protective member (not shown) is moved toward the base plate 216. In use, as the protective member (not shown) is moved toward the base plate 216, the body 222 will be compressed thereby exposing the piercing tips 228a, 228b to allow the tips to penetrate through tissue. A person skilled in the art will appreciate that the compressible body 222 can be formed from a variety of materials. In an exemplary embodiment, the compressible body 222 is formed from a foam, such as a compressible bioabsorbable foam buttress. Exemplary foam materials include, by way of non-limiting example, a lyophilized caprolactone-glycolide open cell foam, or instat lyophilized collagen hemostatic foam.

Figure 1D:
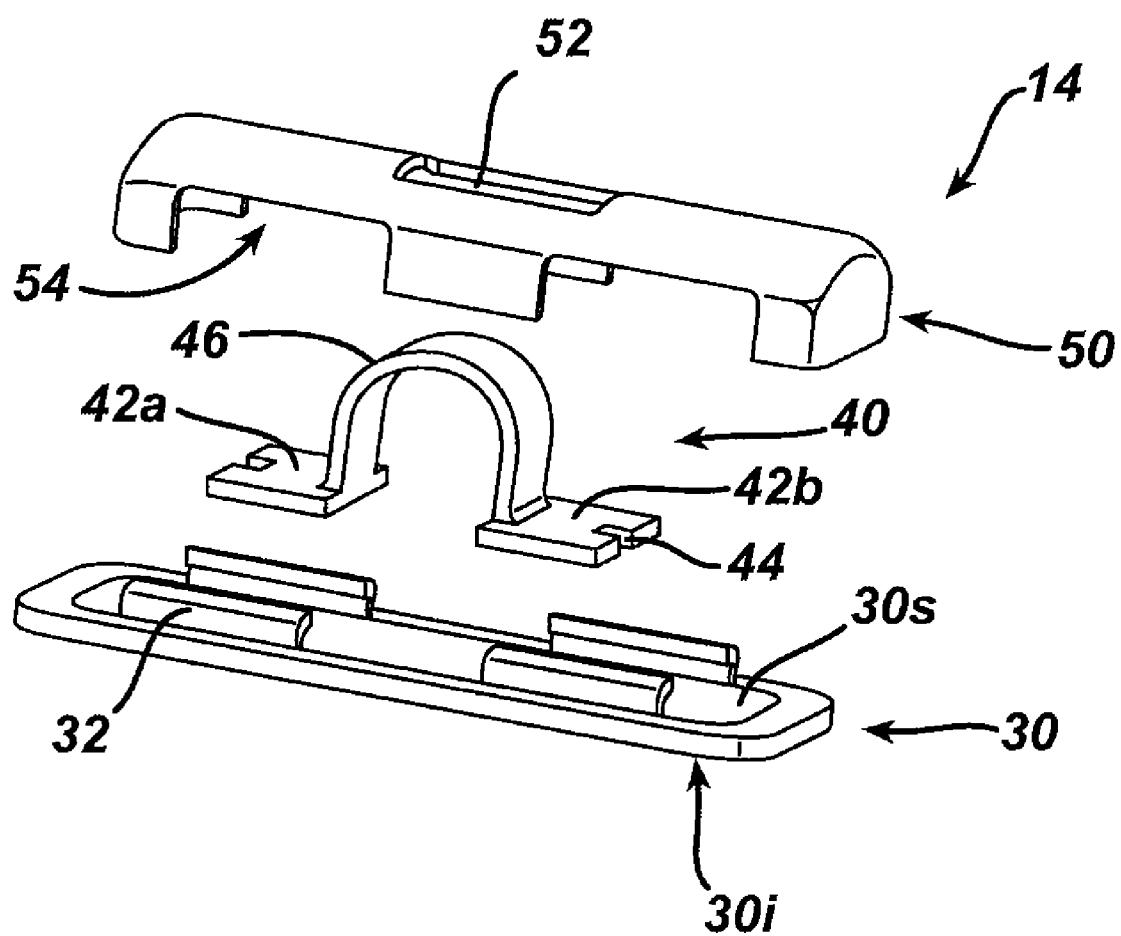
FIG. 1D is an exploded view of the female fastening member of FIG. 1A.

As indicated above, the device 10 can also include a female fastening member 14 designed to mate to the male fastening member 12 to engage tissue therebetween. The female fastening member 14 can have a variety of shapes and configurations, but in an exemplary embodiment, as shown in FIG. 1D, it can include a base plate 30 and a cover plate 50 that form a housing having a similar size and shape as the base plate 16 of the male fastening member 12. The base plate 30 and the cover plate 50 can be mated to one another using a variety of techniques, but in the illustrated embodiment, the base plate 16 includes several locking tabs 32 formed around a perimeter of a superior surface 30s thereof for engaging corresponding recesses 54 formed in the cover plate 50. When mated, the base plate 30 and cover plate 50 form a housing with a height sufficient for receiving the tissue-penetrating members 20a, 20b which extend through first and second holes 34a, 34b in the base plate 16 as the male and female fastening members 12, 14 are mated to one another. As shown in FIG. 1D, the female fastening member 14 can also include a retaining element 40 positioned between the base plate 30 and the cover plate 50 and configured to couple with the tissue-penetrating members 20a, 20b of the male fastening member 12. The retaining element 40 can have first and second tabs 42a, 42b, each with cut-outs 44 adapted to engage the notches 26a, 26b on the first and second tissue-penetrating members 20a, 20b of the male fastening member 12. The tabs 42a, 42b can be biased away from one another and into the notches 26a, 26b by a U-shaped biasing element 46 extending between the tabs 42a, 42b. The U-shaped biasing element 46 can also be configured to release the tissue-penetrating members 20a, 20b of the male fastening member 12. For example, a grasper can be used to compress the sides of the U-shaped biasing element 46 toward one another thereby moving the tabs 42a, 42b toward one another to release the notches 26a, 26b on the first and second tissue-penetrating members 20a, 20b of the male fastening member 12. The female fastening member 14 can thus be separated from the male fastening member 12 if desired. A person skilled in the art will appreciate that other mating elements known in the art can be used to engage the notches 26a, 26b on the tissue-penetrating members 20a, 20b, and that other release mechanisms known in the art can be used to facilitate separation of the male and female fastening members 12, 14.

Figure 1E:
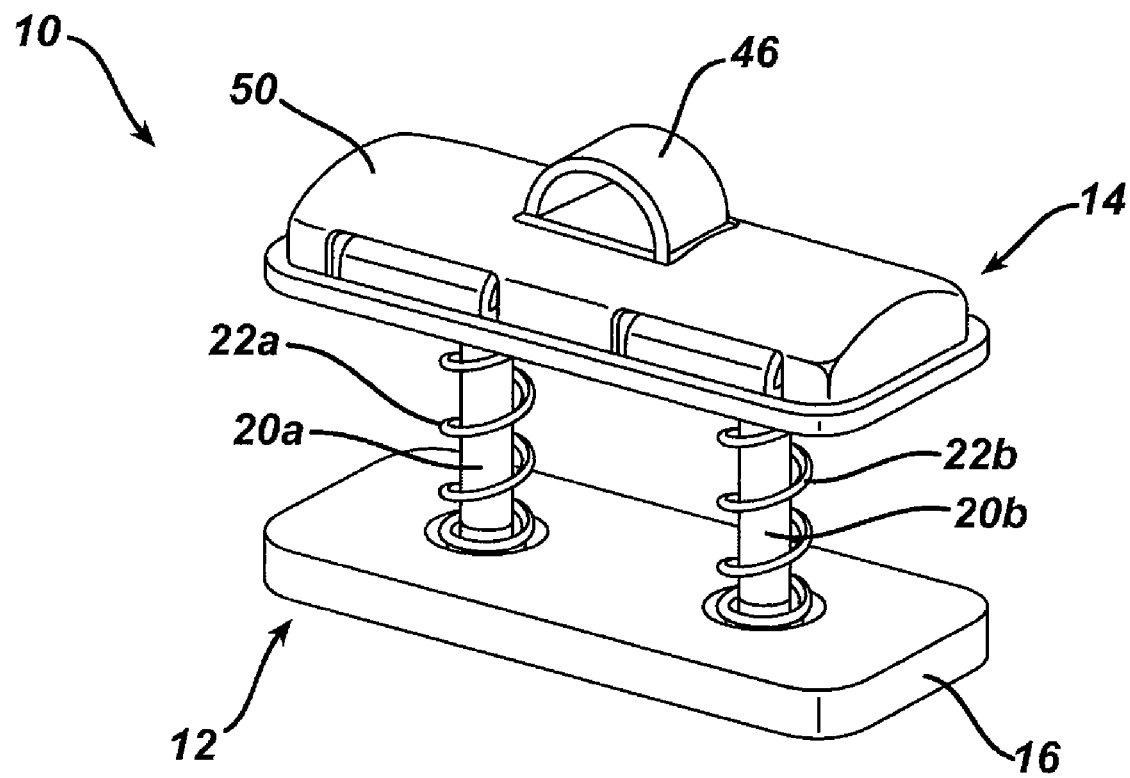
FIG. 1E is a perspective view of the tissue fastening device of FIG. 1A, showing the male and female fastening members mated to one another.

FIG. 1E shows the assembled tissue-fastening device 10. The male fastening member 12 is shown mated with the female fastening member 14. The female fastening member 14 has received the tissue-penetrating members 20a, 20b of the male fastening member 12, which extend through the openings 24a, 24b in the protective member 18 and the holes 34a, 34b in the base plate 30 of the female fastening member 14. The notches 26a, 26b will thus be engaged by the cut-outs 44 in the retaining element 40 of the female fastening member 14. The U-shaped biasing element 46 extends through the opening 52 in the cover plate 50, the sides of which can optionally be compressed so as to release and separate the male and female fastening members 12, 14.

Figure 3:
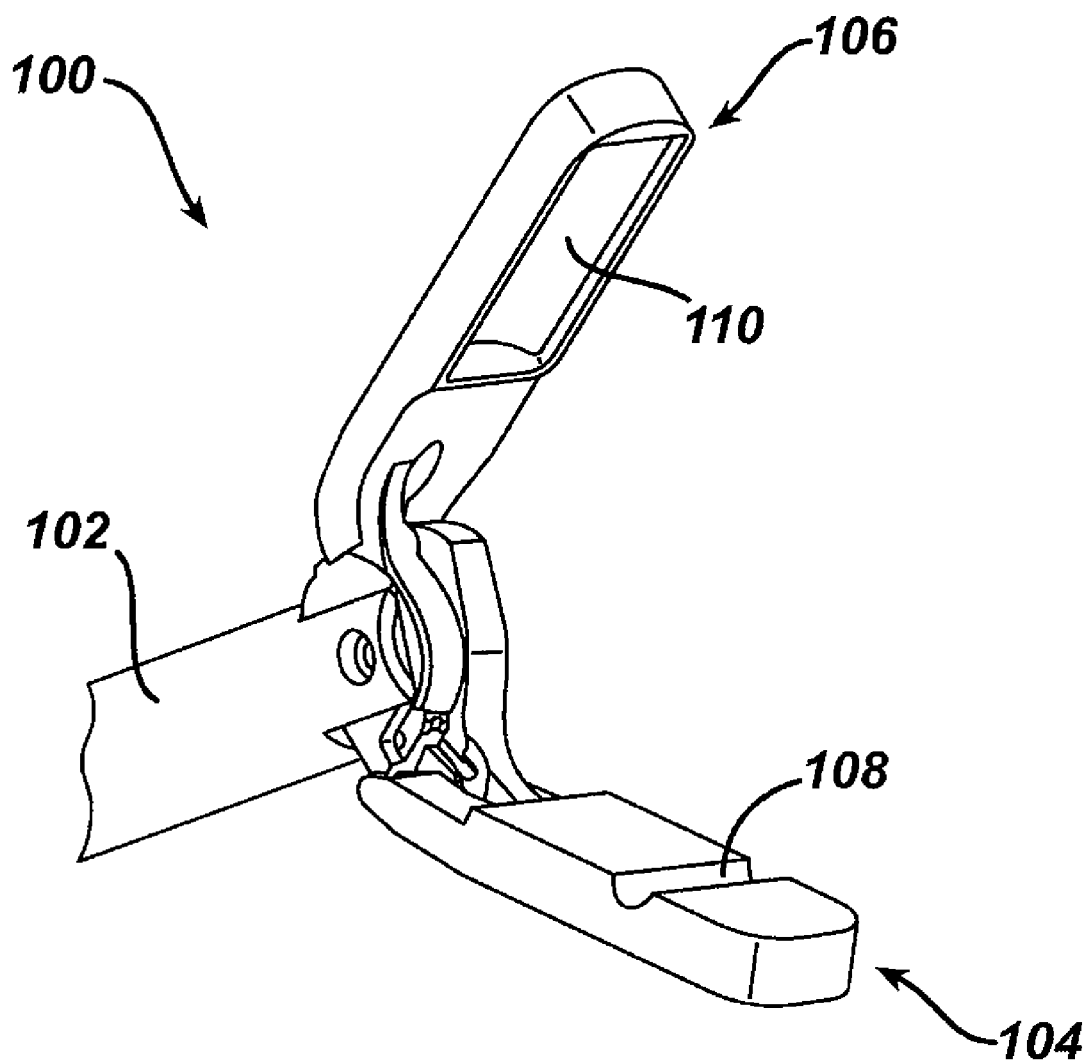
FIG. 3 is a perspective view of first and second jaws of an actuator device.

In use, the tissue-fastening device 10 can be applied with any actuator device known in the art, however, FIG. 3 illustrates a distal portion of one exemplary actuator device 100 configured to apply the tissue-fastening device 10 to tissue. As shown, the actuator device 100 includes a shaft 102 having first and second jaws 104, 106 pivotally coupled to a distal end thereof. While not shown, the device 10 can include a handle that is adapted to move the first and second jaws 104, 106 between an open and closed position. The first and second jaws 104, 106 can generally be configured to receive the male and female fastening members using various mating technique known in the art. In the illustrated embodiment, the first jaw 104 includes a recess 108 formed thereon and configured to seat a corresponding protrusion formed on an inferior surface 16i of the base plate 16 of the male fastening member 12. The recess 108 can be adapted to releasably hold the protrusion of the base plate 16 by way of an interference or compression fit. The second jaw 106 can also include a recess 110 formed therein and configured to receive the cover plate 50 of the female fastening member 14. Again, a compression or interference fit can be used to releasably retain the female fastening member within the second jaw 106. A person skilled in the art will appreciate that other mating techniques known in the art can be used to mate the first and second jaws 104, 106 with the tissue-fastening device 10.

Figure 4A:
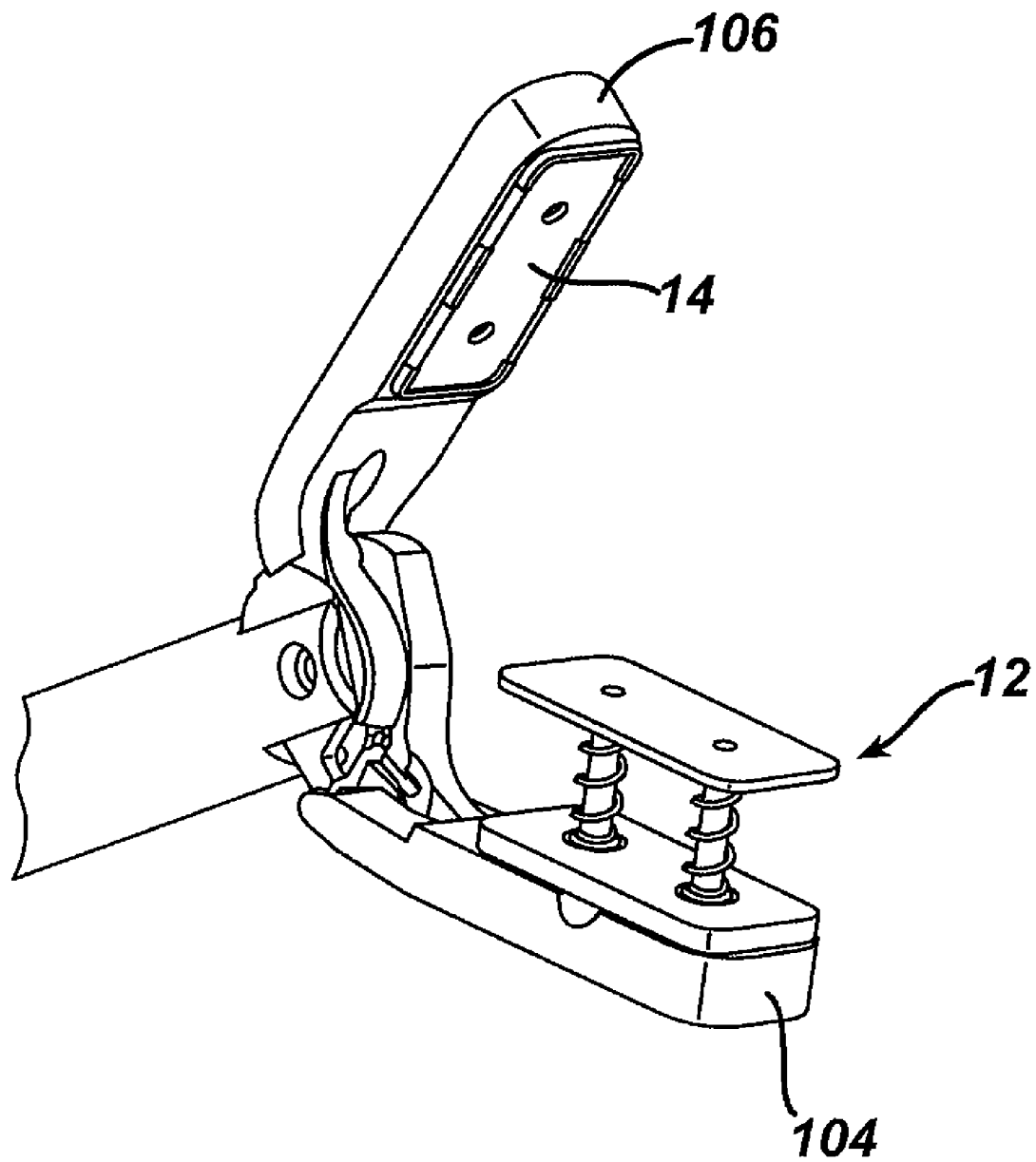
FIG. 4A is a perspective view of the tissue fastening device of FIG. 1A disposed in the jaws of the actuator device of FIG. 3, showing the jaws in an open position.
Figure 4B:
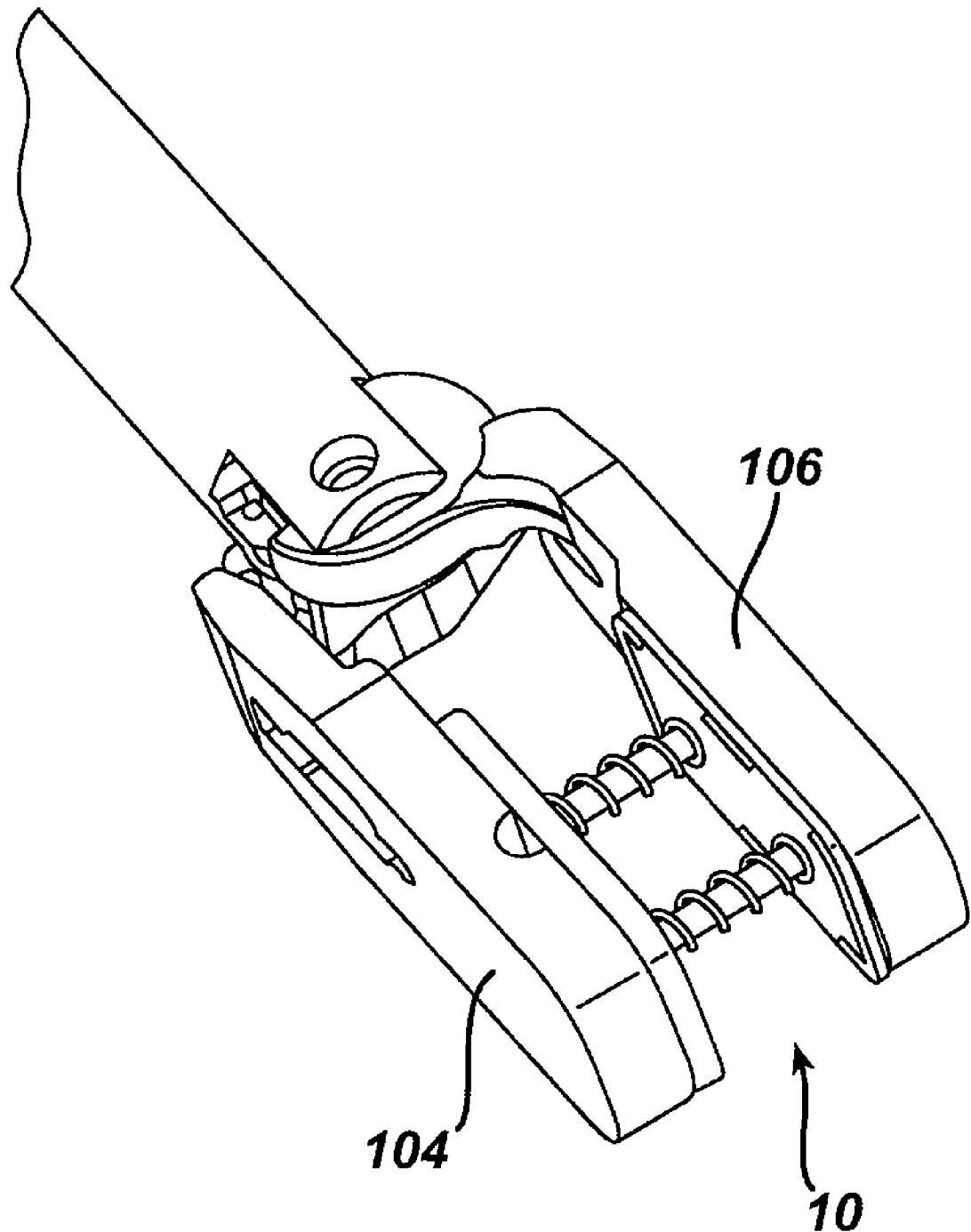
FIG. 4B is a perspective view of the tissue fastening device and jaws of FIG. 4A, showing the jaws in a closed position with the male and female fastening members mated to one another.

FIG. 4A shows the tissue-fastening device 10 disposed within the jaws 104, 106. As shown, the first and second jaws 104, 106 are open for receiving tissue therebetween, and the protective member 18 on the male fastening member 12 is in the open position. The piercing tips 28a, 28b of the first and second tissue-penetrating members 20a, 20b are enclosed within the holes 24a, 24b of the protective member 18 so as to prevent collateral tissue damage during positioning. FIG. 4B illustrates the first and second jaws 104, 106 closed so that the female fastening member 14 has received the first and second tissue-penetrating members 20a, 20b of the male fastening member 12. While not shown, when tissue is engaged between the male fastening member 12 and the female fastening member 14, the protective member 18 will be moved toward the base plate 16 of the male fastening member 12 to compress the biasing element.

Figure 5A:
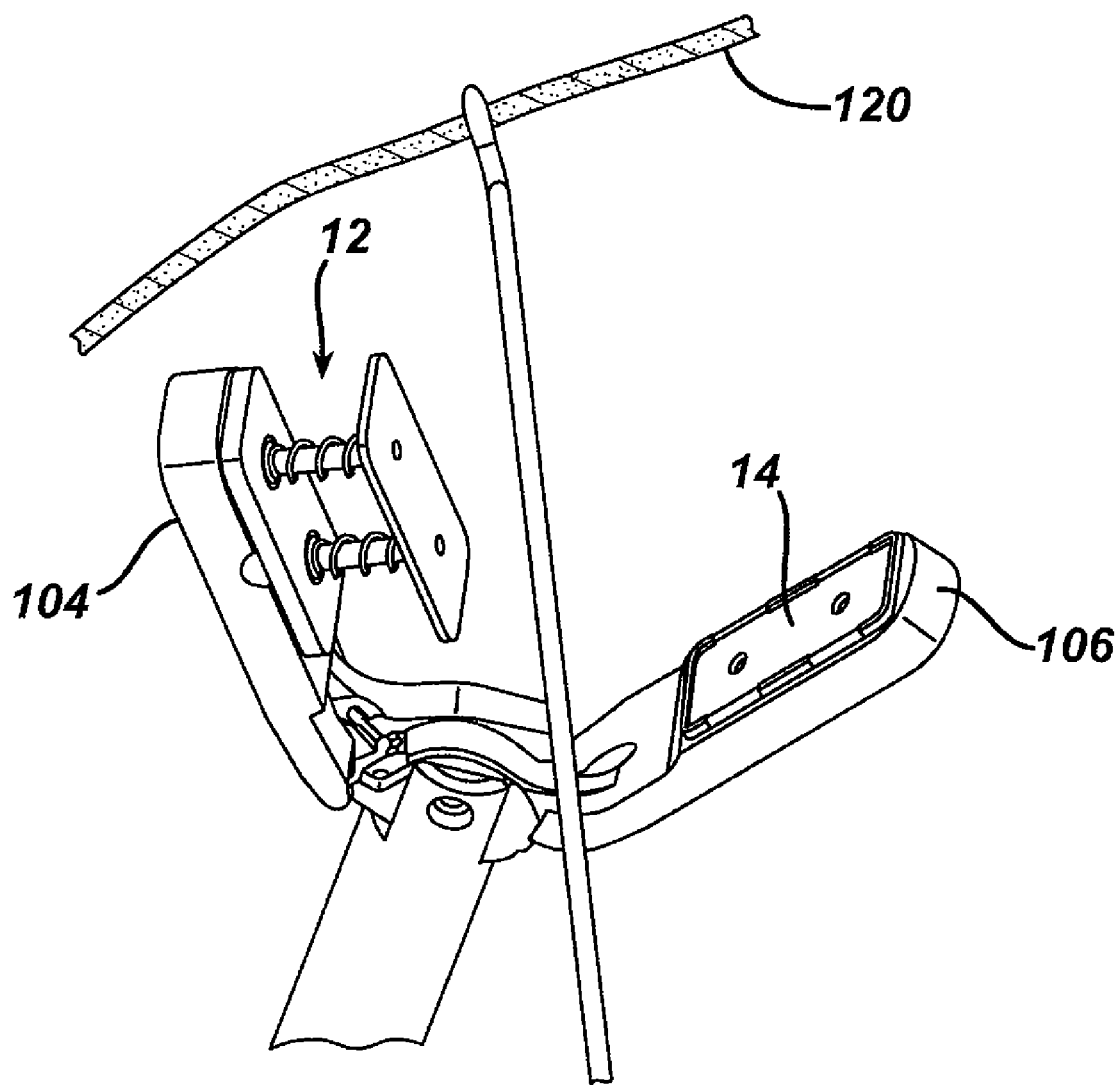
FIG. 5A illustrates the tissue fastening device and jaws of FIG. 4A being inserted into a body cavity and positioned adjacent to tissue to be fastened, showing a grasping device for pulling the tissue into the jaws.

The present invention also provides exemplary methods for fastening tissue. A person skilled in the art will appreciate that the devices described herein can be configured for use in virtually any medical procedure in which it is desirable to attach two tissue surfaces to one another. As shown in FIG. 5A, the male fastening member 12 and female fastening member 14 can be disposed within the first and second jaws 104, 106 of an actuator device 100 for introducing the tissue-fastening device 10 into a body cavity. A person skilled in the art will appreciate that any acceptable method of inserting the actuator device 100 into a body cavity can be used. In one exemplary embodiment, a shaft 102 of the actuator device 100 is flexible to allow the tissue-fastening device 10 to be inserted endoscopically through a natural orifice and body lumen. As the tissue-fastening device 10 is inserted, the protective member 18 is maintained in the open position so that the piercing tips 28a, 28b are enclosed within the holes 24a, 24b located in the protective member 18. This allows the first and second jaws 104, 106 to be positioned around tissue 120 without causing collateral damage. Once the actuator device 100 is inserted into a body cavity and positioned adjacent to tissue to be grasped, a grasper or other technique known in the art can be used to pull the tissue 120 between the first and second jaws 104, 106 of the actuator device 100 so that the male fastening member 12 and female fastening member 14 are on opposed sides of tissue 120 to be fastened, as shown in FIG. 5A. Alternatively, the jaws 104, 106 can merely be positioned around the tissue to be engaged.

Figure 5B:
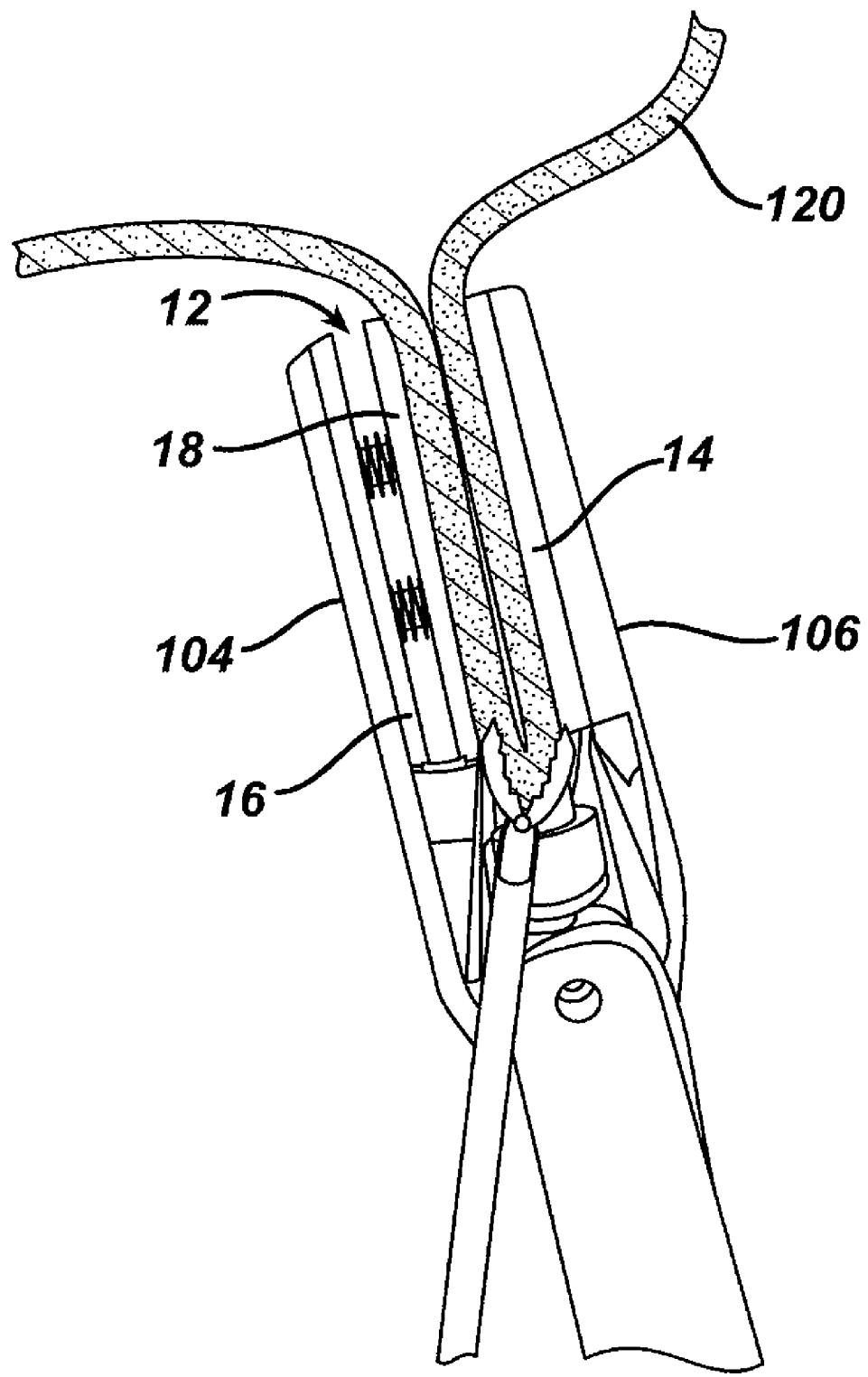
FIG. 5B illustrates the tissue-fastening device and body cavity of FIG. 5A, showing the tissue being engaged between the male fastening member and female fastening member.
Figure 5C:
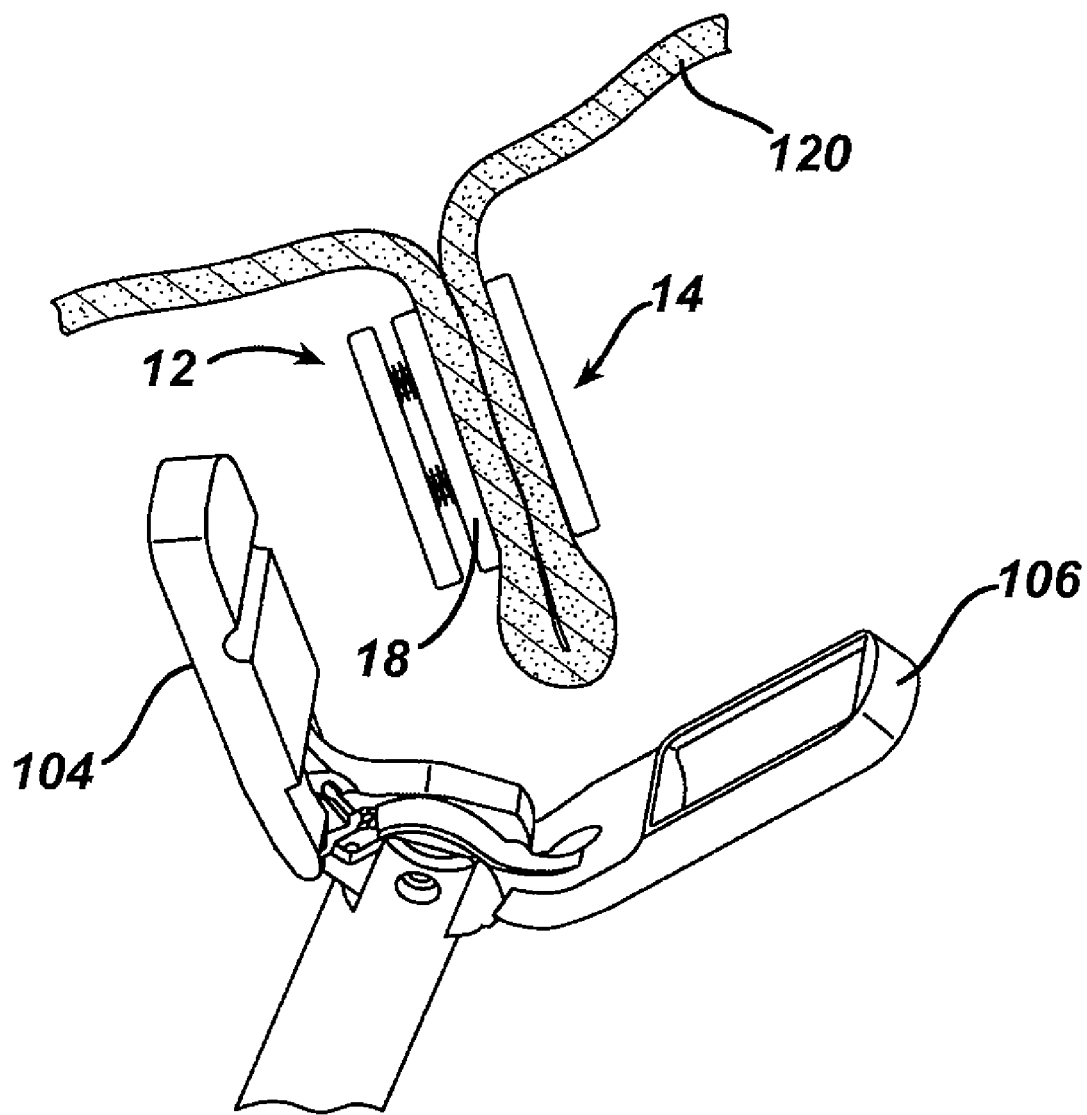
FIG. 5C illustrates the tissue fastening device of FIG. 5B released from the jaws, showing the protective member applying a constant compression force to the engaged tissue.

As the first and second jaws 104, 106 are closed around the tissue 120, the protective member 18 is pressed in a direction towards the base plate 16 exposing the piercing tips 28a, 28b of the first and second tissue-penetrating members 20a, 20b. The tissue-penetrating members 20a, 20b will thus penetrate through the tissue 120 and will eventually extend into the holes 34a, 34b in the female fastening member 14 to mate with the retaining element 40, as shown in FIG. 5B. The notches 26a, 26b on the first and second tissue-penetrating members 20a, 20b will engage the cut-outs 44 in the retaining element 40 to lock the male and female fastening members 12, 14 together and thereby engage tissue between the female fastening member 14 and the protective member 18. Through the biasing element, the protective member 18 can provide a constant compression force to the engaged tissue 120 so as to maintain contact between the tissue surfaces while preventing tissue necrosis. This can be achieved by providing biasing elements having the necessary properties. As shown in FIG. 5C, once the tissue 120 is engaged, the jaws 104, 106 of the actuator device 100 can be opened to release the tissue-fastening device 10, and the actuator device 100 can be withdrawn as the tissue-fastening device 10 remains engaged around the tissue 120.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A fastener, comprising:
    a male fastening member having a substantially straight elongate base plate with first and second posts extending therefrom, each post having a tissue-piercing tip, the first post being positioned adjacent to a first terminal end of the base plate and the second post being positioned adjacent to a second terminal end of the base plate;
    a protective member coupled to the male fastening member and having first and second preformed openings, the protective member being movable between an open position in which the tissue-piercing tips are enclosed within the protective member such that the tissue-piercing tips are prevented from penetrating tissue, and a compressed position in which the tissue-piercing tips are exposed to penetrate tissue;
    a female fastening member configured to receive and enclose the tissue-piercing tips of the first and second posts to mate to the male fastening member to engage tissue therebetween; and
    a biasing element disposed around the first and second posts and extending between the base plate and the protective member, the biasing element configured to bias the protective member with respect to the female member to the open position.

2. The fastener of claim 1, wherein the protective member comprises a plate with first and second bores formed therethrough adapted to receive the first and second posts.

3. The fastener of claim 1, wherein the protective member is adapted to move from the open position to the compressed position when the first and second posts are penetrated through tissue.

4. The fastener of claim 1, wherein the biasing element comprises first and second coil springs.

5. The fastener of claim 1, wherein the biasing element comprises a compressible body surrounding the first and second posts.

6. The fastener of claim 1, wherein the first and second posts extend substantially perpendicular to a surface of the base plate.

7. The fastener of claim 1, further comprising a mating element formed on the first and second posts and adapted to mate with a corresponding mating element formed on the female fastening member.

8. The fastener of claim 1, wherein the female fastening member includes a retaining element configured to engage the first and second posts to secure the male fastening member to the female fastening member.

9. The fastener of claim 8, wherein the retaining element includes first and second arms and a release mechanism extending between the first and second arms, the release mechanism configured to bias the first and second arms into engagement with the first and second posts.

10. The fastener of claim 9, wherein the release mechanism is configured to allow removal of the female fastener from the male fastener.

11. The fastener of claim 1, wherein the elongate base plate has a substantially rectangular shape.

12. A tissue fastener, comprising:
    a base member having first and second tissue-penetrating elements formed thereon and defining a longitudinal axis extending therebetween;
    a protective member movably coupled to the first and second tissue-penetrating elements and adapted to prevent the first and second tissue-penetrating elements from penetrating through tissue until the protective member is advanced against tissue to be penetrated by the first and second tissue-penetrating elements; and
    a closure mechanism matable to the first and second tissue-penetrating elements to engage tissue between the base member and the closure mechanism and having a release mechanism configured to allow removal of the closure mechanism from the first and second tissue-penetrating elements, the release mechanism having a U-shaped biasing element and first and second tabs biased in a direction away from one another along the longitudinal axis of the tissue fastener into engagement with the first and second tissue-penetrating elements and configured to be moved toward one another along the longitudinal axis to release the first and second tissue-penetrating elements.

13. The fastener of claim 12, wherein the protective member comprises a plate with first and second bores formed therethrough and adapted to receive the first and second tissue-penetrating elements.

14. The fastener of claim 13, further comprising a mating element adapted to mate the first and second tissue-penetrating elements.

15. The fastener of claim 12, further comprising a second biasing element configured to bias the protective member to, the first position.

16. The fastener of claim 15, wherein the second biasing element comprises first and second coil springs disposed around the first and second tissue-penetrating elements and extending between the base member and the protective member.

17. The fastener of claim 15, wherein the second biasing element comprises a U-shaped spring mated to and extending between the protective member and the base member.

18. The fastener of claim 15, wherein the second biasing element comprises a compressible body surrounding the first and second tissue-penetrating elements.

19. The fastener of claim 18, wherein the compressible body is adapted to be penetrated by the first and second tissue-penetrating elements when the protective member is moved to the second position.

* * * * *